United States Patent [19]

Krüger et al.

[11] 4,243,404
[45] Jan. 6, 1981

[54] 1,2,3-THIADIAZOLE-3-IN-5-YLIDENE-UREA DERIVATIVES, PROCESS FOR MAKING THE SAME AND COMPOSITIONS CONTAINING THE SAME HAVING GROWTH REGULATING ACTIVITY FOR PLANTS

[75] Inventors: Hans-Rudolf Krüger; Friedrich Arndt; Reinhart Rusch, all of Berlin, Fed. Rep. of Germany

[73] Assignee: Schering Aktiengesellschaft, Berlin and Munich, Fed. Rep. of Germany

[21] Appl. No.: 893,357

[22] Filed: Apr. 4, 1978

[30] Foreign Application Priority Data

Apr. 7, 1977 [DE] Fed. Rep. of Germany ....... 2716324

[51] Int. Cl.³ .................. A01N 47/36; C07D 285/06
[52] U.S. Cl. ........................................... 71/73; 71/76; 71/90; 544/134; 546/209; 546/277
[58] Field of Search ................ 260/306.8 D, 294.8 D, 260/295 E, 293.68; 71/90, 73, 76, 82; 546/209, 277; 544/134; 548/127

[56] References Cited

U.S. PATENT DOCUMENTS

| | | | |
|---|---|---|---|
| 3,565,901 | 2/1971 | Cebalo | 260/293.68 |
| 3,874,873 | 4/1975 | Volpp et al. | 71/90 |
| 3,883,547 | 5/1975 | Schulz et al. | 71/90 |
| 3,954,785 | 5/1976 | Metzger et al. | 71/90 |

Primary Examiner—Alton D. Rollins
Attorney, Agent, or Firm—Michael J. Striker

[57] ABSTRACT

1,2,3-Thiadiazole-3-in-5-ylidene-urea derivative of the formula

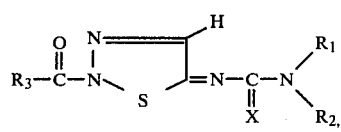

I in which $R_1$ is hydrogen or alkyl which may be substituted in one or several places by oxygen or sulfur and wherein $R_2$ and $R_3$ have the meaning as given in the attached specification and wherein X is oxygen or sulfur. The compounds have properties suited for controlling the natural growth and natural development of plants and in addition have a superior defoliating property without accompanying unpleasant odors.

54 Claims, No Drawings

1,2,3-THIADIAZOLE-3-IN-5-YLIDENE-UREA DERIVATIVES, PROCESS FOR MAKING THE SAME AND COMPOSITIONS CONTAINING THE SAME HAVING GROWTH REGULATING ACTIVITY FOR PLANTS

BACKGROUND OF THE INVENTION

The invention relates to 1,2,3-thiadiazole-3-in-5-ylidene-urea derivatives.

Herbicidal agents on the basis of carbamoylaminothiadiazoles are already known, for instance 2-(N,N-dimethylcarbamoylamino)-5-methylthio-1,3,4-thiadiazole. These are agents which result in destruction of the undesirable plants.

There are furthermore known agents for causing defoliation of plants, for instance tri-n-butyltrithiophosphate (U.S. Pat. No. 2,954,467). This latter compound has not always an adequate activity. Besides, it results in developing unpleasant odors which sometimes annoy the entire environment for days with their smell.

It is therefore an object of the present invention to provide for an agent for the control of the natural growth and development of plants which also can be used as defoliant without any unpleasant accompanying smells.

SUMMARY OF THE INVENTION

The invention resides in a 1,2,3-thiadiazole-3-in-5-ylidene-urea derivative of the formula

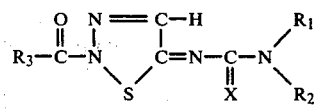

in which $R_1$ is hydrogen or alkyl which may also be substituted in its chain in one or several places by oxygen or sulfur and wherein $R_2$ is (a) alkyl which may be substituted in one or several places in its chain by oxygen or sulfur,
(b) a cycloaliphatic hydrocarbon residue which may be substituted in one or several places by alkyl,
(c) an aromatic hydrocarbon residue which may be substituted in one or several places by alkyl, halogen, alkylthio, alkoxy, trifluoromethyl and/or nitro,
(d) a heterocyclic hydrocarbon residue which contains at least one nitrogen atom in its ring and which may also be substituted, or
(e) wherein $R_1$ and $R_2$ together with the adjoining nitrogen atom form a morpholino-, piperidino- or pyrrolidino group, and wherein $R_3$ is (a) hydrogen,
(b) $C_1$ to $C_{18}$ alkyl which may also be substituted, by halogen or phenyloxy
(c) $C_2$ to $C_8$ alkenyl,
(d) aralkyl wherein alkyl has 1 to 2 carbon atoms,
(e) a $C_5$ to $C_8$ cycloaliphatic hydrocarbon residue which may also be substituted in one or several places by $C_1$ to $C_6$ alkyl,
(f) an aromatic hydrocarbon residue which may also be substituted in one or several places by $C_1$ to $C_6$ alkyl, halogen, $C_1$ to $C_6$ alkoxy, nitro- or trifluoromethyl,
(g) a heterocyclic hydrocarbon residue which may also be substituted,
(h) $C_1$ to $C_6$ alkoxy,
(i) $C_2$ to $C_6$ alkenyl- or alkinyloxy,
(j) aryloxy which may also be substituted,
(k) $C_1$ to $C_4$ alkylthio,
(l) arylthio, or
(m) amino of the formula

in which $R_4$ and $R_5$ are the same or different and are hydrogen, $C_1$ to $C_6$ alkyl or aryl which may also be substituted in one or several places by the same or different substituents selected from the group consisting of $C_1$ to $C_6$ alkyl, halogen, $C_1$ to $C_6$ alkoxy, nitro, and trifluoromethyl, and wherein X is oxygen or sulfur.

The invention also embraces a process for making the compounds and compositions containing the same.

The compounds of the invention have superior growth regulating properties for plants and excel over prior art compounds in their defoliating properties.

This natural growth regulation of the compounds of the invention results in a morphological modification of the plant which can easily be determined by visual observation. These changes may consist in the size, the shape or the color of the plant or any parts thereof.

The effects obtained can generally be designated as retardation. It is believed that the compounds have an effect on the hormone supply of the plants.

In certain kinds of plants this development results in a reduction or obliteration of the apex growth whereby a shorter main stalk or stem and a delayed lateral branching is obtained. These modifications of the natural growth result in smaller, more bushy plants.

The use of the compounds of the invention therefore has surprising technical advantages. Thus, the compounds delay the vegetative growth of the plants which in case of agricultural plants is very often desirable. In addition, it is possible to obtain desirable effects in the plants, as for instance the defoliation of plants, the increased formation of off-shoots, and a shortening of the axial members.

With many plants such as potatoes, sugarcane, sugar beet, grapes, melons, fruit trees and silage plants, it is possible, together with the suppression of the apical growth, to obtain an increase of the carbon hydrate contents of the plants as harvested. In case of fruit and plantation cultures the inhibition of the plant growth on the other hand results in shorter more sturdy twigs, so that the branches are better accessible and the harvesting process is facilitated. In case of grasses there is principally obtained an inhibition of the vertical growth which permits to further space the times for the mowing operations.

One of the specific effects of the invention is the defoliation. It is known among experts that defoliation is not a herbicidal action and that the destruction of the treated plants may even be undesirable because the leaves still stick to the dead plant and the productive plant parts can thus be damaged. The idea of the defoliation rather is to obtain an easier harvesting operation and a harvested product of greater purity. This could be lost by the herbicidal action. It is therefore necessary that the plant remains alive while the leaves separate and drop to the ground. This furthermore permits a further development of the productive plant parts which will prevent a new leaf growth.

The compounds of the invention can preferably be used in mixture with prior art compounds or by successive spraying therewith. Such prior art compounds are for instance:
  auxin,
  α-(2-chlorophenoxy)-propionic acid,
  4-chlorophenoxyacetic acid
  2,4-dichlorophenoxyacetic acid,
  indolyl-3-acetic acid,
  indolyl-3-butyric acid,
  α-naphthyl acetic acid,
  β-naphthoxy acetic acid,
  naphthylacetamide,
  n-m-tolylphthalamido acid,
  gibberellins,
  S,S,S-tri-n-butyl-trithiophosphoric acid ester,
  cytokinines,
  2-chloroethylphosphonic acid,
  2-chloro-9-hydroxyfluorene-9-carboxylic acid,
  2-chloroethyl-trimethylammoniumchloride,
  N,N-dimethylaminosuccinic acid amide,
  2-isopropyl-4-trimethylammonio-5-methylphenyl-piperidine-1-carboxylic acid estermethylchloride,
  phenyl-isopropylcarbamate,
  3-chlorophenyl-isopropylcarbamate,
  ethyl-2-(3-chlorophenylcarbamoyloxy)-propionate,
  maleic acid hydrazide,
  2,3-dichloroisobutyric acid,
  di-(methoxythiocarbonyl)disulfide,
  1,1'-dimethyl-4,4'-bipyridylium-dichloride,
  3,6-endoxohexahydrophthalic acid,
  3-amino-1,2,4-triazole,
  1,2,3-thiadiazolyl-5-yl-urea derivative,
  1-(2-pyridyl)-3-(1,2,3-thiadiazole-5-yl)-urea
  2-butylthio-benzthiazole,
  2-(2-methylpropylthio)-benzthiazole,
  3,4-dichloroisothiazole-5-carboxylic acid,
  2,3-dihydro-5,6-dimethyl-1,4-dithiino-1,1,4,4-tetroxide,
  arsenic acid,
  cacodylic acid,
  chlorates, preferably calcium chlorate, potassium chlorate, magnesium chlorate or sodium chlorate,
  calcium cyanamide,
  potassium iodide,
  magnesium chloride,
  abscisinic acid,
  nonanol.

The activity and speed of action of the compounds can furthermore also be increased by activity increasing additives such as organic solvents, wetting agents and oils. This permits a further reduction of the amounts of the active compounds proper.

The compounds of the invention are preferably used in the form of compositions such as powders, spraying agents, solvents, emulsions or suspensions. There are added liquids and/or solid carrier materials or diluents and, if desired, wetting agents, adhesion promoting agents, emulsifiers and/or dispersants.

Suitable liquid carrier materials are for instance water, aliphatic and aromatic hydrocarbons, cyclohexanone, isophorone, dimethylsulfoxide, dimethylformamide, and furthermore mineral oil fractions.

As solid carrier materials there are suited mineral earths, for instance tonsil, silicagel, talc, kaolin, attaclay, limestone, silicic acid and plant products such as flours.

There may also be added surface active agents as for instance calcium lignosulfonate, polyoxyethylenealkylphenylether, naphthalinesulfonic acids, fatty alcohol sulfates as well as substituted benzosulfonic acids and their salts.

The proportion of active agents in the different compositions may be varied widely. The compositions may for instance contain about 10 to 80% by weight of active agents, 90 to 20% by weight of liquid or solid carrier materials and, if desired, up to 20% by weight of surface active agents in which case the carrier materials should be subject to a corresponding reduction in amounts.

The weight ratio of the individual active agents when used in mixtures with other agents of the prior art should be between about 100:1 and 1:1000, preferably between 10:1 and 1:1000. It depends on the sensitivity and the strength of the plant, the time of application and the climatic conditions and ground composition.

The amounts for regulating the growth of the plants in case of a surface treatment are usually 0.05 to 5 kg of active agent per about 2.5 acres. In specific cases it is possible to exceed these limits upwards or downwards. The manner of growth regulating action depends also on the time of treatment, the type of plants and the concentration.

The compounds of the invention can be applied to different parts of the plants such as the harvested mass, the roots, the stems, the leaves, the blossoms, and the fruits. It is also possible to apply the compounds by spraying in a preemergence or postemergence application. As against various weeds the inhibiting effects may be such that a total obstruction of the development including bushes occurs.

DETAILS OF THE INVENTION AND PREFERRED EMBODIMENTS

Among the compounds of the invention those are preferred in which in the above formula I $R_1$ is hydrogen or alkyl with 1 to 4 carbon atoms, for instance methyl, ethyl, isopropyl, propyl, butyl, and in which $R_2$ is alkyl of 1 to 4 carbon atoms, for instance methyl or ethyl, cycloalkyl of 5 to 8 carbon atoms for instance cyclopentyl, cyclohexyl, methylcyclohexyl or aryl, for instance phenyl, halogenophenyl, $C_1$–$C_4$ alkylphenyl, $C_1$–$C_4$ alkoxyphenyl, nitrophenyl, trifluoromethylphenyl, or $R_2$ is a pyridyl or pyrimidyl residue which is substituted in one or several positions by the same or several substituents selected from the group consisting of $C_1$–$C_4$ alkyl, $C_1$–$C_4$ alkoxy, halogen, nitro and trifluoromethyl.

Among the radicals designated in formula I as $R_3$ there are for instance $C_1$–$C_{18}$ alkyl, like methyl, ethyl, propyl, n-butyl, 1-ethylpropyl, tert-butyl, n-heptyl, n-nonyl, n-undecyl, n-octadecyl, or 3,3-dimethylpropyl; substituted $C_1$–$C_{18}$ alkyl like chloromethyl, fluoromethyl, 2-chloromethyl, 1-chloroethyl, dichloromethyl, trichloromethyl, phenoxymethyl, 1-phenoxyethyl, 2-phenoxyethyl or (2,4-dichlorophenoxy)-methyl; $C_2$–$C_8$ alkenyl, like 2-butenyl, 2-methyl-2-propenyl or propen-1-yl; $C_5$–$C_8$ cycloaliphatic hydrocarbon residues like cyclopentyl, cyclohexyl or methylcyclohexyl; aliphatic-aromatic hydrocarbon residues like benzyl or substituted aliphatic-aromatic hydrocarbon residue like n-chlorobenzyl; aromatic or substituted aromatic hydrocarbon residues like phenyl, 3-chlorophenyl, 2-chlorophenyl, 4-chlorophenyl, 2,4-dichlorophenyl, 2-methylphenyl, 3-methylphenyl, 4-methylphenyl, 3-nitrophenyl, 4-nitrophenyl, 2-methoxyphenyl, 4-methoxyphenyl, 1-naphthyl, 2-naphthyl; 2-furyl; $C_1$-$C_6$ alkoxy like methoxy, ethoxy, propoxy, isopropoxy or n-butoxy; $C_2$-$C_6$ alkenyl- or alkinyloxy like 2-propenyloxy, 2-butenyloxy or 2-propinyloxy; phenoxy or substituted phenyloxy like 4-chlorophenoxy; phenylthio or substituted phenylthio like 4-chlorophenylthio; $C_1$-$C_4$ alkylthio like methylthio, ethylthio or propylthio and amino groups like methylamino, dimethylamino, anilino, N-methylanilino or substituted amino compounds like 4-chloroanilino and wherein X is oxygen or sulfur.

Specific particularly preferred compounds of the invention are for instance the following:

1-(2-acetyl-1,2,3-thiadiazole-3-in-5-ylidene)-3-phenylurea, 5-phenylcarbamoylimino-1,2,3-thiadiazole-3-in-2-carboxylic acid methyl ester, 5-phenylcarbamoylimino-1,2,3-thiadiazole-3-in-2-carboxylic acid ethyl ester, 5-phenylcarbamoylimino-1,2,3-thiadiazole-3-in-2-carboxylic acid isobutyl ester, 5-phenylcarbamoylimino-1,2,3-thiadiazole-3-in-2-carboxylic acid isopropyl ester, 5-phenylcarbamoylimino-1,2,3-thiadiazole-3-in-2-carboxylic acid phenyl ester, 1-(2-chloroacetyl-1,2,3-thiadiazole-3-in-5-ylidine)-3-phenylurea, 5-phenylcarbamoylimino-1,2,3-thiadiazole-3-in-2-thiocarboxylic acid-S-ethyl ester, 1-(2-benzoyl-1,2,3-thiadiazole-3-in-5-ylidene)-3-phenylurea, 3-(2-acetyl-1,2,3-thiadiazole-3-in-5-ylidene)-1-methyl-1-phenylurea, 5-methylphenylcarbamoylimino-1,2,3-thiadiazole-3-in-2-carboxylic acid methyl ester
and
5-methylphenylcarbamoylimino-1,2,3-thiadiazole-3-in-2-thiocarboxylic acid-S-ethyl ester.

PROCESS OF MAKING THE COMPOUNDS

The compounds of the invention can be made in different manners such as for instance the following:

(A) Metal compounds of the general formula

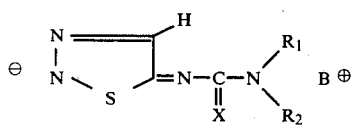
II are reacted with acyl halides $R_3$—CO—Y  III or with isocyanates of the formula $R_5$—N=C=O.  IV (B) (1,2,3-thiadiazole-5-yl)-urea derivatives of the formula

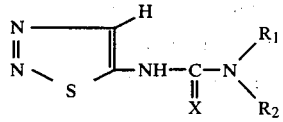
V are reacted in the presence of acid acceptors with acyl halides of the formula $R_3$—CO—Y.  III (C) (1,2,3-thiadiazole-5-yl)-urea derivatives of the formula

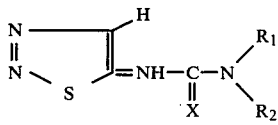
V are reacted with acid anhydrides of the general formula $R_3$—CO—O—CO—$R_3$,  VI which reaction may be carried out in the presence of a catalyst.

In all of the above reactions $R_1$, $R_2$, $R_3$, $R_5$ and X have the same meaning as in above formula I, Y is halogen, preferably chlorine, and B is a univalent metal equivalent, preferably sodium, potassium or lithium.

The reaction may be carried out at a temperature between 0° and 120° C., but preferably is carried out at room temperature. The reactants are used in about equimolar amounts. As reaction media there may be used polar organic solvents. The selection of the solvents or suspension agents depends on the type of acyl halides, the type of acid acceptors and the type of metal compounds.

As solvents or suspension agents there may for instance be used the following: acid nitriles, like acetonitrile, ethers, like tetrahydrofuran and dioxane, acid amines, like dimethylformamide, ketones, like aceton.

As acid acceptors there may be used organic bases such as triethylamine or N,N-dimethylaniline and pyridine bases, or inorganic bases, like oxides, hydroxides, and carbonates of the alkali earth and alkali metals. Liquid bases such as pyridine can simultaneously serve as solvents.

The compounds made by the above process can then be isolated in conventional manner, for instance by distilling them off the solvent at normal or reduced pressure or by precipitation with water.

The compounds of the invention usually are yellowish, non-smelling, crystalline materials which have a low solubility in water and aliphatic hydrocarbons, have a moderate to good solubility in halogenated hydrocarbons like chloroform and carbon tetrachloride, ketones, like acetone, carboxylic acid amides such as dimethylformamide, sulfoxides like dimethylsulfoxide, carboxylic acid nitriles like acetonitrile and lower alcohols such as methanol and ethanol.

As solvents for the recrystallation there may be used e.g. carbon tetrachloride, chloroform, acetonitrile and dimethylformamide.

The starting products for making the compounds of the invention are known.

The following examples will further illustrate the invention

EXAMPLE 1

1-(Acetyl-1,2,3-thiadiazole-3-in-5-ylidene)-3-phenylurea 2.14 ml (0.03 mol) of acetylchloride are added dropwise within 5 minutes at 25° C. to a solution of 5.5 g (0.025 mol) 1-phenyl-3-(1,2,3-thiadiazole-5-yl)-urea in 40 ml pyridine. After standing overnight at room temperature the solution is diluted with icewater. The formed crystals are removed by suction and washed with water and finally dried in a vacuum. Recrystallization from vacuum gives a yield of 5.3 g which is 80.9% of the calculated yield in the form of yellow crystals of an m.p. of 186° C. (decomposed).

EXAMPLE 2

1-(2-chloroacetyl-1,2,3-thiadiazole-3-in-5-ylidene)-3-phenylurea 5.5 g (0.025 mol of 1-phenyl-3-(1,2,3-thiadiazole-5-yl)-urea are added dropwise at room temperature to a solution of 8.55 g (0.05 mol) chloroacetanhydride in 25 ml of acetonitrile. There are then added 3 drops of pyridine and the solution is stirred for 3 hours at room temperature. The strongly yellow crystal slurry is then diluted with icewater and subjected to suction. The crystals obtained are washed with water and finally dried in a vacuum. The recrystallization is effected with acetonitrile. The yield is 6.3 g=85% of the calculated amount in the form of yellow crystals, m.p. 189° C. (decomposed). In an analogous manner there were also obtained the following compounds of the invention:

| Compound No. | Name | Physical constants |
|---|---|---|
| 3 | 5-phenylcarbamoylimino-1,2,3-thiadiazole-3-in-2-carboxylic acid methyl ester | m.p.: 167.5° C. (decomposed) |
| 4 | 5-phenylcarbamoylimino-1,2,3-thiadiazole-3-in-2-carboxylic acid ethyl ester | m.p.: 161.5° C. (decomposed) |
| 5 | 5-phenylcarbamoylimino-1,2,3-thiadiazole-3-in-2-carboxylic acid isobutylester | m.p.: 181° C. (decomposed) |
| 6 | 5-phenylcarbamoylimino-1,2,3-thiadiazole-3-in-2-carboxylic acid isopropyl ester | m.p.: 172° C. (decomposed) |
| 7 | 5-phenylcarbamoylimino-1,2,3-thiadiazole-3-in-2-carboxylic acid phenyl ester | m.p.: 197° C. (decomposed) |
| 8 | 5-phenylcarbamoylimino-1,2,3-thiadiazole-3-in-2-thiocarboxylic acid-S-ethyl-ester | m.p.: 206° C. (decomposed) |
| 9 | 1-(2-benzoyl-1,2,3-thiadiazole-3-in-5-ylidene)-3-phenylurea | m.p.: 210° C. (decomposed) |
| 10 | 1-(2-decanoyl-1,2,3-thiadiazole-3-in-5-ylidene)-3-phenylurea | m.p.: 180° C. (decomposed) |
| 11 | 1-(2-phenoxyacetyl-1,2,3-thiadiazole-3-in-5-ylidene)-3-phenylurea | m.p.: 197° C. (decomposed) |
| 12 | 1-phenyl-3-(2-propionyl-1,2,3-thiadiazole-3-in-5-ylidene)-urea | m.p.: 198° C. (decomposed) |
| 13 | 1-(2-(3-chloropropionyl)-1,2,3-thiadiazole-3-in-5-ylidene)-3-phenylurea | m.p.: 194° C. (decomposed) |
| 14 | 1-(2-butyryl-1,2,3-thiadiazole-3-in-5-ylidene)-3-phenylurea | m.p.: 195° C. (decomposed) |
| 15 | 1-(2-isobutyrl-1,2,3-thiadiazole-3-in-5-ylidene)-3-phenylurea | m.p.: 197° C. (decomposed) |
| 16 | 1-(2-pentanoyl-1,2,3-thiadiazole-3-in-5-ylidene)-3-phenylurea | m.p.: 195° C. (decomposed) |
| 17 | 1-phenyl-3-(2-pivaloyl-1,2,3-thiadiazole-3-in-5-ylidene)-urea | m.p.: 184° C. (decomposed) |
| 18 | 1-(2-(2-chlorobenzoyl)-1,2,3-thiadiazole-3-in-5-ylidene)-3-phenylurea | m.p.: 202° C. (decomposed) |
| 19 | 5-phenylcarbamoylimino-1,2,3-thiadiazole-3-in-2-carboxylic acid butyl ester | m.p.: 152° C. (decomposed) |
| 20 | 5-phenylcarbamoylimino-1,2,3-thiadiazole-3-in-2-carboxylic acid dimethylamide | m.p.: 210° C. (decomposed) |
| 21 | 1-(2-(3-chlorobenzoyl)-1,2,3-thiadiazole-3-in-5-ylidene)-3-phenylurea | m.p.: 183° C. (decomposed) |
| 22 | 1-(2-acetyl-1,2,3-thiadiazole-3-in-5-ylidene)-3-methyl-3-phenylurea | m.p.: 155°–56° C. |
| 23 | 5-methylphenylcarbamoylimino-1,2,3-thiadiazole-3-in-2-carboxylic acid methyl ester | m.p.: 137° C. (decomposed) |
| 24 | 5-methylphenylcarbamoylimino-1,2,3-thiadiazole-3-in-2-carboxylic acid ethyl ester | m.p.: 98°–99° C. (decomposed) |
| 25 | 1-(2-benzoyl-1,2,3-thiadiazole-3-in-5-ylidene)-3-methyl-3-phenylurea | m.p.: 131°–33° C. |
| 26 | 5-methylphenylcarbamoylimino-1,2,3-thiadiazol-3-in-2-thiocarboxylic acid-S-ethyl ester | m.p.: 80°–81° C. |
| 27 | 5-methylphenylcarbamoylimino-1,2,3-thiadiazol-3-in-2-carboxylic acid propyl ester | m.p.: 102° C. (decomposed) |
| 28 | 5-methylphenylcarbamoylimino-1,2,3-thiadiazole-3-in-2-carboxylic acid isopropyl ester | m.p.: 117° C. (decomposed) |
| 29 | 5-methylphenylcarbamoylimino-1,2,3-thiadiazole-3-in-2-carboxylic acid phenyl ester | m.p.: 139°–40° C. (decomposed) |
| 30 | 5-methylphenylcarbamoyl- | m.p.: |

-continued

| Compound No. | Name | Physical constants |
|---|---|---|
| | imino-1,2,3-thiadiazole-3-in-2-thiocarboxylic acid-S-methyl ester | 110°–111° C. |
| 31 | 5-methylphenylcarbamoyl-imino-1,2,3-thiadiazole-3-in-2-thio carboxylic acid-S-propyl ester | m.p.: 97°–98° C. |
| 32 | 5-methylphenylcarbamoyl-imino-1,2,3-thiadiazole-3-in-2-thio carboxylic acid-S-phenyl ester | m.p.: 137°–38° C. |
| 33 | 1-methyl-1-phenyl-3-(2-pivaloyl-1,2,3-thiadiazole-3-in-5-yliden)-urea | m.p.: 119°–20° C. |
| 34 | 1-(2-isopropionyl-1,2,3-thiadiazole-3-in-5-yliden)-3-methyl-3-phenylurea | m.p.: 82°–84° C. |
| 35 | 1-(2-(2-chlorobenzoyl)-1,2,3-thiadiazole-3-in-5-yliden)-3-methyl-3-phenylurea | m.p.: 112°–13° C. |
| 36 | 5-phenylcarbamoyl-imino-1,2,3-thiadiazole-3-in-2-carboxylic acid allyl ester | m.p.: 160° C. (decomposed) |
| 37 | 1-(2-acetyl-1,2,3-thiadiazole-3-in-5-ylidene)-3-(2-pyridyl)-urea | m.p.: 194° C. (decomposed) |
| 38 | 5-(2-pyridylcarbamoyl-imino)-1,2,3-thiadiazole-3-in-2-thiocarboxylic acid-S-methylester | m.p.: 230° C. (decomposed) |
| 39 | 5-(2-pyridylcarbamoyl-imino)-1,2,3-thiadiazole-3-in-2-thiocarboxylic acid-S-ethyl ester | m.p.: 233° C. (decomposed) |
| 40 | 1-(2-butyryl-1,2,3-thiadiazole-3-in-5-ylidene)-3-(2-pyridyl)-urea | m.p.: 201° C. (decomposed) |
| 41 | 5-phenylcarbamoyl-imino-1,2,3-thiadiazole-3-in-2-carboxylic acid propyl ester | m.p.: 157°–58° C. |
| 42 | 5-phenylcarbamoylimino-1,2,3-thiadiazole-3-in-2-thiocarboxylic acid-S-propyl ester | m.p.: 199° C. (decomposed) |
| 43 | 1-(2-(3,4-dichlorobenzoyl)-1,2,3-thiadiazole-3-in-5-ylidene)-3-phenylurea | m.p.: 210.5° C. (decomposed) |
| 44 | 1-methyl-1-phenyl-1-(2-propionyl-1,2,3-thiadiazole-3-in-5-ylidene)-urea | m.p.: 109°–10° C. |
| 45 | 5-(2-pyridylcarbamoyl-imino)-1,2,3-thiadiazole-3-in-2-carboxylic acid methyl ester | m.p.: 182° C. (decomposed) |
| 46 | 5-(2-pyridylcarbamoyl-imino)-1,2,3-thiadiazole-3-in-2-carboxylic acid ethyl ester | m.p.: 200° C. (decomposed) |
| 47 | 5-phenylcarbamoylimino- | m.p.: |
| | 1,2,3-in-2-thiocarboxylic acid-2-phenyl ester | 227° C. (decomposed) |
| 48 | 1-(2-(2-furoyl)-1,2,3-thiadiazole-3-in-5-ylidene)-3-phenylurea | m.p.: 218° C. (decomposed) |
| 49 | 1-(2-(3-methylbutyryl)-1,2,3-thiadiazole-3-in-5-ylidene)-3-phenylurea | m.p.: 192° C. (decomposed) |
| 50 | 5-phenylcarbamoylimino-1,2,3-thiadiazole-3-in-2-thiocarboxylic acid-S-methylester | m.p.: 227° C. (decomposed) |
| 51 | 1-(2-(4-chlorobenzoyl)-1,2,3-thiadiazole-3-in-5-ylidene)-3-(2-pyridyl)-urea | m.p.: 220° C. (decomposed) |
| 52 | 1-(2-acetyl-1,2,3-thiadiazole-3-in-5-ylidene)-3-phenyl-thiourea | m.p.: 206° C. (decomposed) |
| 53 | 1-(2-benzoyl-1,2,3-thiadiazole-3-in-5-ylidene)-3-(2-pyridyl)-urea | m.p.: 215° C. (decomposed) |
| 54 | 1-(2-cyclohexylcarbonyl-1,2,3-thiadiazole-3-in-5-ylidene)-3-phenylurea | m.p.: 192°–194° C. |
| 55 | 1-(2-acetyl-1,2,3-thiadiazole-3-in-5-ylidene)-3,3-dimethylurea | m.p.: 186°–187° C. |
| 56 | 1-(2-benzoyl-1,2,3-thiadiazole-3-in-5-ylidene)-3,3-dimethylurea | m.p.: 177°–177.5° C. |
| 57 | 5-(phenylcarbamoylimino)-1,2,3-thiadiazole-3-in-2-carboxylic acid hexyl ester | m.p.: 148°–149° C. |
| 58 | 1-(2-crotonyl-1,2,3-thiadiazole-3-in-5-ylidene)-3-urea | m.p.: 174° C. (decomposed) |
| 59 | 1-(2-(4-chlorobenzoyl)-1,2,3-thiadiazole-3-in-5-ylidene)-3-phenylurea | m.p.: 207°–209° C. (decomposed) |
| 60 | 5-phenylcarbamoylimino-1,2,3-thiadiazole-3-in-2-carboxylic acid-sec.-butyl-ester | m.p.: 134°–135° C. |
| 61 | 5-dimethylcarbamoylimino-1,2,3-thiadiazole-3-in-2-carboxylic acid methylamide | m.p.: 157°–158° C. |
| 62 | 5-(2-pyridylcarbamoylimino)-1,2,3-thiadiazole-3-in-2-carboxylic acid dimethyl amide | m.p.: 199° C. (decomposed) |

USES AND APPLICATIONS

The following examples will further illustrate the activity and different uses of the compounds of the invention.

EXAMPLE 3

In a hothouse potted bush beans (*phaseolus vulgaris*) were treated with the inventive compounds listed in the table below with varying amounts of 0.1 and 3 kg of active agent per about 2.5 acres as also indicated below. In the same manner were treated soy beans (*glycine maxima*). The treatment was effected with the bush beans after formation of the primary leaves and with the soy beans at the inception of the development of the first trilobed leaf group. The active agent was used in the form of a 20% concentration spray powder and in an aqueous suspension, the amount of liquid being 500 liters per spray mass. The growth regulating effect was determined two weeks after treatment by measuring the length of the first internodium. The results of the measurement were considered in relation to the untreated control plants and were calculated as percentage growth delay.

As appears from the following table I a growth regulating effect was obtained with the compounds of the invention through a wide range of concentration without causing any burn damage in the leaves.

EXAMPLE 4

In a hothouse agricultural plants, to wit, seed tomatoes, potatoes and sorghum and furthermore the weed *cyperus esculentus* were treated in a postemergence application with a dosage of 0.3 kg of active agent per about 2.5 acres using the compound indicated in Table 2. The active agent was formulated as a 20% concentration spray powder and was applied in an aqueous suspension in an amount of liquid of 500 liters of spray per about 2.5 acres. The effect was evaluated two weeks after treatment. In the evaluation 10=without injury to the plants and 0=total growth inhibition.

As appears from the table surprisingly no effect was found in the agricultural plants, while the weed *cyperus esculentus* was completely destroyed in its development. This weed is distributed around the globe together with cyperus rotundus and is very difficult to suppress. The treatment with the compound of the invention made a further vegetative or generative spreading of the weed entirely impossible.

TABLE I

| Compounds of the Invention | Amount kg/about 2.5 acres | Growth delay in % relative to untreated | |
|---|---|---|---|
| | | bush bean | soy bean |
| 1-(acetyl-1,2,3-thiadiazole-3-in-5-ylidene)-3-phenyl-urea | 0.1 | 40 | 45 |
| | 3 | 60 | 70 |
| 5-phenylcarbamoylimino-1,2,3-thiadiazole-3-in-2-carboxylic acid methyl ester | 0.1 | 35 | 30 |
| | 3 | 60 | 60 |
| 5-phenylcarbamoylimino-1,2,3-thiadiazole-3-in-2-carboxylic acid ethyl ester | 0.1 | 45 | 50 |
| | 3 | 65 | 70 |
| 5-phenylcarbamoylimino-1,2,3-thiadiazole-3-in-2-carboxylic acid isobutyl ester | 0.1 | 25 | 25 |
| | 3 | 60 | 60 |
| 5-phenylcarbamoylimino-1,2,3-thiadiazole-3-in-2-carboxylic acid isopropyl ester | 0.1 | 25 | 30 |
| | 3 | 60 | 60 |
| 1-(2-chloroacetyl-1,2,3-thiadiazole-3-in-5-ylidene)-3-phenyl-urea | 0.1 | 30 | 30 |
| | 3 | 65 | 65 |
| 5-phenylcarbamoylimino-1,2,3-thiadiazole-3-in-2-thiocarboxylic acid-S-ethyl ester | 0.1 | 25 | 25 |
| | 3 | 60 | 60 |
| 1-(2-benzoyl-1,2,3-thiadiazole-3-in-5-ylidene)-3-phenylurea | 0.1 | 30 | 25 |
| | 3 | 65 | 60 |
| 1-phenyl-3-(2-propionyl-1,2,3-thiadiazole-3-in-5-ylidene)-urea | 0.1 | 30 | 30 |
| | 3 | 50 | 50 |
| 1-(2-(3-chloropropionyl)-1,2,3-thiadiazole-3-in-5-ylidene)-3-phenylurea | 0.1 | 25 | 25 |
| | 3 | 55 | 55 |
| 1-(2-butyryl-1,2,3-thiadiazole-3-in-5-ylidene)-3-phenylurea | 0.1 | 35 | 35 |
| | 3 | 65 | 45 |
| 1-(2-isobutyryl-1,2,3-thiadiazole-3-in-5-ylidene)-3-phenyl-urea | 0.1 | 20 | 20 |
| | 3 | 60 | 60 |
| 1-(2-pentanoyl-1,2,3-thiadiazole-3-in-5-ylidene)-3-phenyl-urea | 0.1 | 20 | 35 |
| | 3 | 60 | 55 |
| 1-phenyl-3-(2-pivaloyl)-1,2,3-thiadiazole-3-in-5-ylidene)-urea | 0.1 | 35 | 30 |
| | 3 | 55 | 55 |
| 5-phenylcarbamoylimino-1,2,3-thiadiazole-3-in-2-carboxylic acid butyl ester | 0.1 | 25 | 25 |
| | 3 | 50 | 50 |
| 5-phenylcarbamoylimino-1,2,3-thiadiazole-3-in-2-carboxylic acid dimethylamide | 0.1 | 25 | 20 |
| | 3 | 45 | 50 |
| 5-methylphenylcarbamoylimino 1,2,3-thiadiazole-3-in-2-carboxylic acid methyl ester | 0.1 | 20 | 60 |
| | 3 | 30 | 70 |

TABLE II

| Compound of the invention | potato | seed tomato | sorghum | cyperus esculentus |
|---|---|---|---|---|
| 1-(2-acetyl-1,2,3-thiadiazole-3-in-5-ylidene(-3-methyl-3-phenyl-urea | 10 | 10 | 10 | 0 |
| not treated | 10 | 10 | 10 | 10 |

EXAMPLE 5

Growing cotton plants in the stage of 7 to 8 developed foliage leaves were treated with the compounds indicated in Table 3 at the dosage also indicated in tests repeated four times. The amount of water was 500 liters per 2.5 acres. After a few days the percentage of the dropped leaves was determined and indicated as defoliation percentage.

TABLE III

| Compound of the invention | active agent kg/about 2.5 acres | % defoliation |
|---|---|---|
| 1-(2-acetyl-1,2,3-thiadiazole-3-in-5-ylidene)-3-phenylurea | 0.05 | 53.3 |
| 1-(2-chloroacetyl-1,2,3-thiadiazole-3 in-5-ylidene)-3-phenylurea | 0.05 | 66.7 |
| Comparison compound (U.S. Pat. No. 2,954,407) tri-n-butyl-trithiophosphate | 0.05 | 33.3 |

As appears from this table and also from the following examples the compounds of the invention have a faster or stronger action as the prior art comparison compounds.

EXAMPLE 6

Growing cotton plants in the stage of 7 to 8 developed genuine foliage leaves were treated with the compounds and the concentrations indicated in Table 4 below in tests which were repeated four times. The amount of water used was 500 liters per about 2.5 acres. The percentage of the dropped leaves was determined after a few days as the percentage defoliation.

TABLE IV

| | active agent kg/about 2.5 acres | % defoliation |
|---|---|---|
| Compound of the invention | | |
| 5-phenylcarbamoylimino-1,2,3-thiadiazole-3-in-2-carboxylic acid methyl ester | 0.05 | 87.1 |
| | 0.5 | 100 |
| 5-phenylcarbamoylimino-1,2,3-thiadiazole-3-in-2-carboxylic acid iso-butyl ester | 0.05 | 67.7 |
| | 0.5 | 100 |
| 5-phenylcarbamoylimino-1,2,3-thiadiazole-3-in-2-carboxylic acid iso-propyl ester | 0.05 | 90.3 |
| | 0.5 | 93.6 |
| 5-phenylcarbamoylino-1,2,3-thiadiazole-3-in-2-carboxylic acid phenyl ester | 0.05 | 90.3 |
| | 0.5 | 93.6 |
| Comparison compound (U.S. Pat. No. 2,954,467) tri-n-butyl-trithiophosphate | 0.05 | 6.4 |
| | 0.5 | 51.6 |

EXAMPLE 7

Young hibiscus plants in the stage of 8 to 11 leaves were treated in the same manner as stated in Example 6. The results appear from the following table.

TABLE V

| | active agent kg/about 2.5 acres | % defoliation |
|---|---|---|
| Compound of the invention | | |
| 1-(acetyl-1,2,3-thiadiazole-3-in-5-ylidene)-3-phenyl-urea | 0.05 | 83.3 |
| 5-phenylcarbamoylimino-1,2,3-thiadiazole-3-in-2-carboxylic acid ethyl ester | 0.05 | 83.3 |
| 1-(2-chloroacetyl-1,2,3-thiadiazole-3-in-5-ylidene)-3-phenylurea | 0.05 | 94.6 |
| 5-phenylcarbamoylimino-1,2,3-thiadiazole-3-in-2-thiocarboxylic acid-S-ethyl ester | 0.05 | 56.8 |
| 1-(2-benzoyl-1,2,3-thiadiazole-3-in-5-ylidene)-3-phenylurea | 0.05 | 83.8 |
| 1-(2-decanoyl-1,2,3-thiadiazole-3-in-5-ylidene)-3-phenylurea | 0.05 | 86.5 |
| 1-(2-phenoxyacetyl-1,2,3-thiadiazole-3-in-5-ylidene)-3-phenyl-urea | 0.05 | 78.4 |
| Comparison compound (U.S. Pat. No. 2,954,467) tri-n-butyl-trithiophosphate | 0.05 | 0 |
| | 0.5 | 18.9 |

EXAMPLE 8

Young hibiscus plants in the stage of 9 to 12 leaves were treated in the same manner as in Example 6. The results appear from the following table.

TABLE VI

| Compound of the invention | active agent kg/about 2.5 acres | % defoliation |
|---|---|---|
| 1-(2-(3-chloropropionyl)-1,2,3-thiadiazole-3-in-5-lyidene-phenylurea | 0.05 | 81.4 |
| 1-(2-(2-chlorobenzoyl)-1,2,3-thiadiazole-3-in-5-ylidene-phenyl-urea | 0.05 | 51.2 |
| 5-phenylcarbamoylimino-1,2,3-thiadiazole-3-in-2-carboxylic acid dimethylamide | 0.05 | 23.3 |
| 1-(2-acetyl-1,2,3-thiadiazole-3-in-5-ylidene)-3-methyl-3-phenylurea | 0.05 | 46.5 |
| 5-methylphenylcarbamoylimino-1,2,3-thiadiazole-3-in-2-carboxylic acid methyl ester | 0.05 | 62.8 |
| 5-methylphenylcarbamoylimino-1,2,3-thiadiazole-3-in-2-thiocarboxylic acid-S-ethylester | 0.05 | 81.4 |
| Comparison compound (U.S. Pat. No. 2,954,467) tri-n-butyl-trithiophosphate | 0.05 | 2.4 |
| | 0.5 | 52.4 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

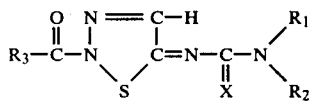

wherein $R_1$ is hydrogen or $C_1$–$C_2$ alkyl;

$R_2$ is $C_1$–$C_4$ alkyl, $C_5$–$C_8$ cycloalkyl, or phenyl or pyridyl optionally substituted in one or more positions by the same or different substituents selected from the group consisting of $C_1$–$C_4$ alkyl, $C_1$–$C_4$ alkoxy, halogen, nitro and $CF_3$;

$R_3$ is hydrogen, $C_1$–$C_{18}$ alkyl which may also be substituted by halogen or phenyloxy, $C_1$–$C_6$ alkoxy, $C_3$–$C_8$ alkenyl, $C_3$–$C_6$ alkenyloxy, $C_3$–$C_6$ alkinyloxy, $C_5$–$C_8$ cycloalkyl optionally substituted by one or more $C_1$–$C_6$ alkyl, $C_1$–$C_4$ alkylthio, an aromatic residue selected from the group consisting of phenyl, naphthyl, phenylthio, phenyloxy and phenylalkyl, having up to two carbons in the alkyl moiety, said aromatic residue being optionally substituted in the aromatic moiety by one or more substituents which are the same or different and are selected from the group consisting of $C_1$–$C_2$ alkyl, $C_1$–$C_6$ alkoxy, halogen, nitro and $CF_3$, furyl, or an amino group of the formula

wherein $R_4$ and $R_5$ are the same or different and are hydrogen or $C_1$–$C_6$ alkyl, phenyl, optionally substituted by one or more substituents which are the same or different and are selected from the group consisting of $C_1$–$C_6$ alkyl, $C_1$–$C_6$ alkoxy, nitro, halogen and $CF_3$; and X is oxygen or sulfur.

2. The compound of claim 1 which is 1-(acetyl-1,2,3-thiadiazole-3-in-5-ylidene)-3-phenylurea.

3. The compound of claim 1 which is 1-(2-chloroacetyl-1,2,3-thiadiazole-3-in-5-ylidene)-3-phenylurea.

4. The compound of claim 1 which is 5-phenylcarbamoylimino-1,2,3-thiadiazole-3-in-2-carboxylic acid methylester.

5. The compound of claim 1 which is 5-phenylcarbamoylimino-1,2,3-thiadiazole-3-in-2-carboxylic acid ethylester.

6. The compound of claim 1 which is 5-phenylcarbamoylimino-1,2,3-thiadiazole-3-in-2-carboxylic acid isobutylester.

7. The compound of claim 1 which is 5-phenylcarbamoylimino-1,2,3-thiadiazole-3-in-2-carboxylic acid isopropylester.

8. The compound of claim 1 which is 5-phenylcarbamoylimino-1,2,3-thiadiazole-3-in-2-carboxylic acid phenylester.

9. The compound of claim 1 which is 5-phenylcarbamoylimino-1,2,3-thiadiazole-3-in-2-thiocarboxylic acid-S-ethylester.

10. The compound of claim 1 which is 1-(2-benzoyl-1,2,3-thiadiazole-3-in-5-ylidene)-3-phenylurea.

11. The compound of claim 1 which is 1-(2-decanoyl-1,2,3-thiadiazole-3-in-5-ylidene)-3-phenylurea.

12. The compound of claim 1 which is 1-(2-phenoxyacetyl-1,2,3-thiadiazole-3-in-5-ylidene)-3-phenylurea.

13. The compound of claim 1 which is 1-phenyl-3-(2-propionyl-1,2,3-thiadiazole-3-in-5-ylidene)-urea.

14. The compound of claim 1 which is 1-(2-(3-chloropropionyl)-1,2,3-thiadiazole-3-in-5-ylidene)-3-phenylurea.

15. The compound of claim 1 which is 1-(2-butyryl-1,2,3-thiadiazole-3-in-5-ylidene)-3-phenylurea.

16. The compound of claim 1 which is 1-(2-isobutyryl-1,2,3-thiadiazole-3-in-5-ylidene)-phenylurea.

17. The compound of claim 1 which is 1-(2-pentanoyl-1,2,3-thiadiazole-3-in-5-ylidene)-phenylurea.

18. The compound of claim 1 which is 1-phenyl-3-(2-pivaloyl-1,2,3-thiadiazole-3-in-5-ylidene)-urea.

19. The compound of claim 1 which is 1-(2-(2-chlorobenzoyl)-1,2,3-thiadiazole-3-in-5-ylidene)-3-phenylurea.

20. The compound of claim 1 which is 5-phenylcarbamoylimino-1,2,3-thiadiazole-3-in-2-carboxylic acid butylester.

21. The compound of claim 1 which is 5-phenylcarbamoylimino-1,2,3-thiadiazole-3-in-2-carboxylic acid dimethylamide.

22. The compound of claim 1 which is 1-(2-(3-chlorobenzoyl)-1,2,3-thiadiazole-3-in-5-ylidene)-3-phenylurea.

23. The compound of claim 1 which is 1-(2-acetyl-1,2,3-thiadiazole-3-in-5-ylidene)-3-methyl-3-phenylurea.

24. The compound of claim 1 which is 1-(2-benzoyl-1,2,3-thiadiazole-3-in-5-ylidene)-3-methyl-3-phenylurea.

25. The compound of claim 1 which is 1-methyl-1-phenyl-3-(2-pivaloyl-1,2,3-thiadiazole-3-in-5-ylidene)-urea.

26. The compound of claim 1 which is, 1-(2-(2-chlorobenzoyl)-1,2,3-thiadiazole-3-in-5-ylidene)-3-methyl-3-phenylurea.

27. The compound of claim 1 which is 5-phenylcarbamoylimino-1,2,3-thiadiazole-3-in-2-carboxylic acid allylester.

28. The compound of claim 1 which is 1-(2-acetyl-1,2,3-thiadiazole-3-in-5-ylidene)-3-(2-pyridyl)-urea.

29. The compound of claim 1 which is 5-(2-pyridyl-carbamoylimino)-1,2,3-thiadiazole-3-in-2-thiocarboxylic acid-S-methylester.

30. The compound of claim 1 which is 5-(2-pyridyl-carbamoylimino)-1,2,3-thiadiazole-3-in-2-thiocarboxylic acid-S-ethylester.

31. The compound of claim 1 which is 1-(2-butyryl-1,2,3-thiadiazole-3-in-5-ylidene)-3-(2-pyridyl)-urea.

32. The compound of claim 1 which is 5-phenylcarbamoylimino-1,2,3-thiadiazole-3-in-2-carboxylic acid propylester.

33. The compound of claim 1 which is 5-phenylcarbamoylimino-1,2,3-thiadiazole-3-in-2-thiocarboxylic acid-S-propylester.

34. The compound of claim 1 which is 1-(2-(3,4-dichlorobenzoyl)-1,2,3-thiadiazole-3-in-5-ylidene)-3-phenylurea.

35. The compound of claim 1 which is 1-methyl-1-phenyl-1-(2-propionyl-1,2,3-thiadiazole-3-in-5-ylidene)-urea.

36. The compound of claim 1 which is 5-(2-pyridyl-carbamoylimino)-1,2,3-thiadiazole-3-in-2-carboxylic acid methyl ester.

37. The compound of claim 1 which is 5-(2-pyridyl-carbamoylimino)-1,2,3-thiadiazole-3-in-2-carboxylic acid ethyl ester.

38. The compound of claim 1 which is 5-phenylcarbamoylimino-1,2,3-thiocarboxylic acid-S-phenylester.

39. The compound of claim 1 which is 1-(2-(2-furoyl)-1,2,1-thiadiazole-3-in-5-ylidene)-3-phenylurea.

40. The compound of claim 1 which is 1-(2-(3-methyl-butyryl)-1,2,3-thiadiazole-3-in-5-ylidene)-3-phenylurea.

41. The compound of claim 1 which is 5-phenylcarbamoylimino-1,2,3-thiadiazole-3-in-2-thiocarboxylic acid-S-methylester.

42. The compound of claim 1 which is 1-(2-(4-chlorobenzoyl)-1,2,3-thiadiazole-3-in-5-ylidene)-3-(2-pyridyl)-urea.

43. The compound of claim 1 which is 1-(2-acetyl-1,2,3-thiadiazole-3-in-5-ylidene)-3-phenyl-thiourea.

44. The compound of claim 1 which is 1-(2-benzoyl-1,2,3-thiadiazole-3-in-5-ylidene)-3-(2-pyridyl)-urea.

45. The compound of claim 1 which is 1-(2-cyclohexylcarbonyl-1,2,3-thiadiazole-3-in-5-ylidene)-3-phenylurea.

46. The compound of claim 1 which is 1-(2-acetyl-1,2,3-thiadiazole-3-in-5-ylidene)-3,3-dimethylurea.

47. The compound of claim 1 which is 1-(2-benzoyl-1,2,3-thiadiazole-3-in-5-ylidene)-3,3-dimethylurea.

48. The compound of claim 1 which is 5-(phenylcarbamoylimino)-1,2,3-thiadiazole-3-in-2-carboxylic acid hexylester.

49. The compound of claim 1 which is 1-(2-(4-chlorobenzoyl)-1,2,3-thiadiazole-3-in-5-ylidene)-3-phenylurea.

50. The compound of claim 1 which is 5-phenylcarbamoylimino-1,2,3-thiadiazole-3-in-2-carboxylic acid-sec.-butylester.

51. The compound of claim 1 which is 5-dimethylcarbamoylimino-1,2,3-thiadiazole-3-in-2-carboxylic acid methylamide.

52. The compound of claim 1 which is 5-(2-pyridyl-carbamoylimino)-1,2,3-thiadiazole-3-in-2-carboxylic acid dimethylamide.

53. A composition having growth regulating activity for plants, the said composition comprising about 10 to 80% by weight of the active agents of claim 1, about 90 to 20% by weight of the liquid or solid carrier material in which latter percentage there may be included 20% by weight of surface active agents.

54. A process for defoliating plants and/or increasing the formation of off-shoots, the said process comprising applying to the plants a composition as defined in claim 53.

* * * * *